(12) United States Patent
Klaveness et al.

(10) Patent No.: US 6,303,101 B1
(45) Date of Patent: *Oct. 16, 2001

(54) BISMUTH COMPOUNDS

(75) Inventors: Jo Klaveness, Oslo; Arne Berg, Sandvika, both of (NO); Torsten Almen, Falsterbo (SE); Klaes Golman, Rungsted Kyst (DK); Michael Droege, Livermore; Shi-bao Yu, Campbell, both of CA (US)

(73) Assignee: Nycomed Imaging AS, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/473,100

(22) Filed: Dec. 28, 1999

Related U.S. Application Data

(63) Continuation of application No. 09/369,694, filed on Aug. 6, 1999, now abandoned, which is a continuation of application No. 08/875,305, filed on Oct. 22, 1997, now Pat. No. 6,117,412, which is a continuation of application No. PCT/GB96/00183, filed on Jan. 26, 1996, which is a continuation-in-part of application No. 08/486,225, filed on Jun. 7, 1995, now Pat. No. 5,817,289.

(30) Foreign Application Priority Data

Jan. 26, 1995 (GB) .................................................. 9501560

(51) Int. Cl.$^7$ .................................................. A61K 49/00
(52) U.S. Cl. ..................... 424/9.1; 424/1.11; 424/1.65; 424/9.3; 424/9.4; 556/30
(58) Field of Search ................... 424/1.11, 1.37, 424/1.65, 1.81, 1.85, 9.1, 9.3, 9.36, 9.4, 9.45, 9.451, 9.44, 9.42, 9.5; 534/7; 556/10–16, 1, 28, 30, 64, 70, 71, 76

(56) References Cited

U.S. PATENT DOCUMENTS

| | | |
|---|---|---|
| 3,239,411 | 3/1966 | Leebrick . |
| 3,247,050 | 4/1966 | Leebrick . |
| 3,466,366 | 9/1969 | Leebrick . |
| 3,753,990 | 8/1973 | Curry . |
| 3,824,307 | 7/1974 | Curry . |
| 3,890,242 * | 6/1975 | Curry et al. .......................... 252/107 |
| 4,153,685 | 5/1979 | Serfontein . |
| 4,588,589 | 5/1986 | Sheth et al. . |
| 4,647,447 | 3/1987 | Gries et al. . |
| 4,652,519 | 3/1987 | Warschawsky et al. . |
| 4,687,659 | 8/1987 | Quay . |
| 4,826,673 | 5/1989 | Dean et al. . |
| 5,008,256 | 4/1991 | Clitherow . |
| 5,013,560 | 5/1991 | Stentz et al. . |
| 5,229,418 | 7/1993 | Collington et al. . |
| 5,273,984 | 12/1993 | Clitherow . |
| 5,417,958 * | 5/1995 | Deutsch et al. ..................... 424/9.42 |
| 5,482,699 | 1/1996 | Shah . |
| 5,482,700 * | 1/1996 | Deutsch et al. ................... 424/9.364 |
| 5,730,953 | 3/1998 | Suzuki et al. . |
| 5,817,289 * | 10/1998 | Klaveness et al. ................. 424/1.11 |
| 6,117,412 * | 9/2000 | Klaveness et al. ................. 424/1.11 |

FOREIGN PATENT DOCUMENTS

| | | |
|---|---|---|
| 809388 | 5/1974 | (BE) . |
| 2216725 | 10/1973 | (DE) . |
| 0 0217 577 | 9/1986 | (EP) . |
| 0 230 893 | 1/1987 | (EP) . |
| 0 445 743 | 9/1991 | (EP) . |
| 0 480 691 | 4/1992 | (EP) . |
| 0 0533 281 | 9/1992 | (EP) . |
| 0 716 091 | 8/1994 | (EP) . |
| 1003685 | 9/1965 | (GB) . |
| 1341331 | 12/1973 | (GB) . |
| 2 248 185 | 1/1992 | (GB) . |
| 2 262 036 | 6/1993 | (GB) . |
| 63-225381 | 9/1988 | (JP) . |
| WO 89/00557 | 1/1989 | (WO) . |
| WO 89/03219 | 4/1989 | (WO) . |
| WO 91/03241 | 3/1991 | (WO) . |
| WO 92/01457 | 2/1992 | (WO) . |
| WO 92/17215 | 10/1992 | (WO) . |
| WO 93/02713 | 2/1993 | (WO) . |
| WO 95/06053 | 3/1995 | (WO) . |
| WO 96/16677 | 6/1996 | (WO) . |
| WO 96/16678 | 6/1996 | (WO) . |
| 81/7456 | 4/1983 | (ZA) . |

OTHER PUBLICATIONS

Ashana, A., "Reactions of triphenyl antimony, bismuth and their dibromides with pentacholorophenol and pentachlorothiophenol", Chemical Abstracts, Organometallics, vol. 121, 1994, 157769.

Sharutin et al., "Reactions of Vanadocene and Cobaltocene with Dichlorotriphenyl–Antimony and with Dichlorotriphenylbismuth", J. of General Chem., USSR, vol. 61, No. 6–1357–1359, Jun. 1991.

Suzuki et al., "Ultrasonic Reaction of Triarylbismuthines and Trarylstibines with Iodosylbenzene", Tetrahedron Letters, vol. 35, No. 44, pp. 8197–8200, 1994.

\* cited by examiner

Primary Examiner—Dameron L. Jones
(74) Attorney, Agent, or Firm—Fish & Richardson P.C.

(57) ABSTRACT

The use in diagnostic imaging, in particular X-ray, MRI, ultrasound and scintigraphy, of contrast agents comprising bismuth clusters and/or organic bismuth compounds, and contrast media containing such bismuth compounds. The bismuth compounds are also useful in therapy, in particular as antimicrobial agents and antiulcer agents. Novel bismuth compounds are also disclosed.

6 Claims, No Drawings

BISMUTH COMPOUNDS

This is a continuation of U.S. Ser. No. 09/369,694, filed Aug. 6, 1999, which is a continuation of U.S. Ser. No 08/875,305, filed Jul. 23, 1997, now U.S. Pat. No. 6,117,412, which is a continuation of Internation Patent application No. PCT/GB96/00183, with an international filing data of Jan. 26, 1996, now WO 96/22994, which is a continuation-in-part of U.S. Ser. No. 08/486,225, filed Jun. 7, 1995, issued on Oct. 6, 1998 as U.S. Pat. No. 5,817,289, which all claim priority from Great Britain 9501560.8, filed Jan. 26, 1995.

The present invention relates to the use in diagnostic imaging, in particular X-ray, MRI, ultrasound and scintigrapny, of contrast agents comprising bismuth clusters and/or organic bismuth compounds, and to contrast media containing such bismuth compounds. Another aspect of the present invention is the use of the bismuth compounds in therapy, in particular as antiulcer agents.

All diagnostic imaging is based on the achievement of different signal levels from different structures within the body. Thus in X-ray imaging, for example, for a given body structure to be visible in the image the X-ray attenuation by that structure must differ from that of the surrounding tissues. The difference in signal between the body structure and its surroundings is frequently termed contrast and much effort has been devoted to means of enhancing contrast in diagnostic imaging since the greater the contrast between a body structure and its surroundings the higher the quality of the images and the greater their value to the physician performing the diagnosis. Moreover, the greater the contrast the smaller the body structures that may be visualized in the imaging procedure, i.e. increased contrast can lead to increased spatial resolution.

The diagnostic quality of images is strongly dependent on the inherent noise level in the imaging procedure—the ratio of the contrast level to the noise level can thus be seen to represent an effective diagnostic quality factor for diagnostic images.

Achieving improvement in such a diagnostic quality factor has long been and still remains an important goal. In techniques such as X-ray and ultrasound, one approach to improve the diagnostic quality factor has been to introduce contrast enhancing materials, contrast agents, into the body region being imaged.

Thus in X-ray, for instance, early examples of contrast agents were insoluble inorganic barium salts which enhanced X-ray attenuation in the body zones into which they distributed. More recently the field of X-ray contrast agents has been dominated by soluble iodine containing compounds such as those markedet by Nycomed AS under the trade names Omnipaque® and Visipaue®.

Much recent work on X-ray contrast agents has concentrated on aminopolycarboxylic acid (APCA) chelates of heavy metal ions and, recognising that effective imaging of many body sites requires localization at the body sites in question of relatively high concentrations of the metal ions, there have been suggestions that polychelants, that is substances possessing more than one separate chelant moiety, might be used to achieve this.

Various bismuth compounds have been suggested in the prior art as X-ray absorbing agents. Other prior art documents focus on the use of metal chelates in diagnostic imaging, mainly in MRI. In addition, bismuth compounds have a long history in therapeutic medicine specially in treatment of gastrointestinal diseases such as ulcers. Although antiulcer agents such as the $H_2$-antagonists cimetidine and ranitidine, and more recently proton pump inhibitors such as omeprazole, have been developed, there is still medical use of bismuth compounds in ulcer treatment.

The most frequently used bismuth compounds as gastrointestinal drugs today are bismuth subnitrate and bismuth subsalicylate. Bismuth subnitrate or bismuth hydroxide nitrate oxide $(Bi_5O(OH)_9(NO_3)_4$ is prepared by hydrolysis of bismuth nitrate and is practically insoluable in water. It is usually used as a suspension (milk of bismuth). Bismuth subnitrate is also used topically in lotions and ointments. Bismuth subsalicylate or basic bismuth salicylate $(C_7H^5BiO_4)$ is also practically insoluble in water and is administered as a suspension or in the form of tablets. Products containing bismuth subsalicylate are used against indigestion, nausea and diarrhea. As an antidiarmheal agent it shows good activity against Salmonella with less activity versus *E. coli*.

Several bismuth compounds are known to be biologically active and have been suggested as active ingredients in various drug formulations. Organobismuth compounds can be used as antibacterial agents, for example against infections caused by highly resistant gram-negative bacteria (U.S. Pat. No. 3,466,366 of M&T Chem Inc); a protein-type bismuth complex is suggested for treatment of inflammation and infections in the gastrointestinal system in U.S. Pat. No. 4,153,685 (Schering Corp); bismuthyl prostanoate derivatives for ulcer control are suggested in BE 809388 (Aries R); phenylbismuth bis(2-pyridinethiol) 1-oxide as an antibacterial and antifungal agent is disclosed in U.S. Pat. No. 3,824,307 (Procter & Gamble Co); an antiinflammatory and antiulcer bismuth composition containing a mixture of trivalent bismuth, water-soluble protein, an organic acid anion and an alkali in ZA 8107456 (Schering Corp); bismuth subsalicylate in combination with other agents in a synergistic formulation for diarrhoea treatment in U.S. Pat. No. 4,588,589 (Richardson Vicks); treatment of non-ulcer dyspepsia associated with *Campylobacter pyloridis* infection with bismuth salts such as tripotassium dicitrato-bismuthate in WO 89/03219 (Borody T. J.); organo-bismuth compounds useful as anti-coccidium agents for poultry, and as insecticides in J63225391 (Nitto Kasei and Shionogi); pharmaceutical compositions for treatment of gastrointestinal disorders associated with *Campylobacter pylori* infections comprising a pharmaceutically acceptable bismuth compound and first and second antibiotic or antimicrobial agents in EP 439453 (Capability Services et al.); salts formed between rantidine and bismuth carboxylic acid complexes for treatment of gastrointestinal disorders in U.S. Pat. No. 5,008,256 (Glaxo); further salts formed between an $H_2$-receptor antagonist and a complex of bismuth with a carboxylic acid with activity against gastrointestinal conditions and aginst *Campylobacter pylori* in U.S. Pat. No. 5,273,984 (Glaxo); a suspension for oral administration comprising a bismuth containing pharmaceutical agent, benzoic acid and sorbic acid, polymer and water for use against various gastrointestinal disorders in U.S. Pat. No. 5,013,560 (Procter & Gamble); furan derivatives with bismuth carboxylic acid complexes for treatment of various gastrointestinal disorders including activity against *Heliobacter pylori* infections in WO 92/01457 (Evans B. K. et al.); salts of ranitidine with a bismuth carboxylate complex and alkali salt for treatment of various gastrointestinal disorders in GB 2248185 (Glaxo); and ranitidine bismuth citrate and non-steroidal anti-inflammatory drugs for the treatment of inflammation diseases in GB 2262036 (Glaxo).

Finally, WO 95/06053 discloses certain substituted triphenyl bismuth compounds as X-ray contrast agents.

We have now found that certain bismuth compounds give particularly effective contrast enhancement when used as contrast agents. Some of these compounds also can be used in the treatment of various gastrointestinal disorders.

Thus, one aspect of this invention is a diagnostic imaging contrast medium comprising a covalent non-cluster type bismuth compound. Such medium may be used for contrast enhancement in diagnostic imaging, in particular x-ray, MRI, ultrasound imaging and scintigraphy.

For X-ray or ultrasound imaging it is preferred that the compounds comprise two or more heavy atoms where at least one of the heavy atoms is bismuth. For the sake of clarity, the word "heavy atom" means a bromine atom or an atom with atomic number higher than 49.

For MRI the compounds would comprises bismuth and one or more MR active atoms. For the sake of clarity, the words "MR active atom" means an atom that directly or indirectly affects the MR signal. Typical MR active atoms include for example manganese, gadolinium, dysprosium, iron and fluorine.

The invention provides for example diagnostic imaging contrast media comprising a physiologically tolerable molecule of anyu of formulae I–IV,

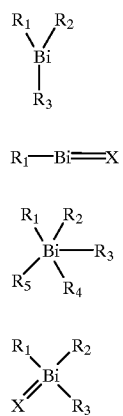

where the groups $R_1$–$R_5$ may be the same or different and are defined as any croup forming a hydrolyticaliy stable bond to bismuth. Typical $R_{1-5}$ groups are preferably aryl groups substituted with one or more heavy atoms, preferably Bi and I. X is O, S or $NR_6$ where $R_6$ is lower alkyl, for example $C_{1-4}$-alkyl, substituted lower alky, or an aryl group.

Viewed from another aspect, the invention provides a diagnostic imaging contrast medium comprising a non-covalent non-cluster type bismuth compound, with the proviso that the bismuth compound contains at least one further heavy atom.

The further heavy atom in such non-covalent non-cluster type compounds may be covalently or non-covalently bonded and may, for example, be an iodine atom. The compound may contain more than one non-covalently bonded bismuth atom, for example 2 or 3 such atoms or even 10 or more such atoms.

Viewed from another aspect, the invention provides a diagnostic imaging contrast medium comprising a physiologically tolerable multinuclear bismuth complex of formula V, $$(M_mB_nA_p)_xL_y \quad (V)$$

where $M_mB_nA_p$ is a multinuclear entity where each M which may be the same or different is a contrast enhancing heavy metal atom and at least one M is Bi (and preferably each M is Bi) and each M is covalently bonded to at least one atom B when n is non-zero; each B which may be the same or different is a non-metal bridging atom covalently bonded to at least two M atoms and optionally to further atoms; each A which may be the same or different is a non-metal non-bridging atom covalently bonded to an M atom; each L which may be the same or different is a ligand co-ordinately bonded to at least one Bi atom; m is a positive integer of value 2 or greater; n, p and y are independently zero or positive integers provided that n and p are not simultaneously zero; x is a positive integer; or a physiologically tolerable salt thereof, together with at least one pharmaceutical excipient.

Viewed from another aspect, the invention also provides the use of bismuth compounds as defined above for the manufacture of contrast media for use in imaging of the human or non-human body.

Viewed from a still further aspect, the invention provides a method of generating an image of a human or non-human animal, preferably mammalian, body which method comprises administering to said body a physiologically tolerable contrast enhancing amount of a bismuth compound as defined above and generating an image of at least part of said body into which said agent distributes, e.g. by X-ray, MRI or ultrasound imaging or scintigraphy.

Viewed from a still further aspect the invention also provides a diagnostic imaging contrast medium comprising a bismuth compound as defined above together with at least one sterile pharmaceutical carrier or excipient.

Viewed from a still further aspect the invention also provides the use of the cluster and covalent non-cluster bismuth compounds as defined above for the manufacture of therapeutic agents for treatment of gastrointestinal disorders, for example caused by *Heliobantpr pylori*.

Viewed from a still further aspect, the invention provides a method of treating a gastrointestinal disorder, for example caused by *Heliobacter pylori*, of a human or non-human animal, preferably mammalian, body which method comprises administering to said body a physiologically tolerable dose of a cluster or covalent non-cluscer bismuth compound as defined above.

The bismuth compounds defined above have particular potential as contrast agents since the compounds have a relative high concentration of heavy elements including bismuth. The use of these compounds enables a high ratio of contrast enhancing atom to overall structure volume to be achieved. Thus by increasing the relative content of contrast enhancing atoms in this way the total cuantity of the contrast agent necessary in order to achieve the same contrast effect may be reduced and thus problems associated with contrast agent solubility or toxicity or osmolality or with contrast medium viscosity may also be reduced.

As mentioned above, it is preferred that the bismuth compounds of the invention comprise two or more contrast enhancing atoms. Both the covalent bismuth molecules and multinuclear cluster chelates also contain further atoms which may have little or no contrast enhancing effect but which may for example function as bridging atoms binding the contrast enhancing atoms together in a cluster (See WO 92/17215 for further examples of these types of structures). Other non-contrast active atoms in the contrast agent function for example as detoxification groups, as solubilizing groups, in groups for targeting of the bismuth atom and the other contrast-active atoms to the area of interest, or the non-contrast active atoms help to stabilize the covalent molecule or chelate against hydrolysis and metabolism.

The bismuth compounds described above may, as pointed out above, be used in various modalities in medical imaging and in certain specific therapeutic fields. Some bismuth compounds are active in more than one modality. The choice of modality should be carefully taken into consideration in design of the agent. For example if the agent is intended for use in MRI, MR active elements such as fluorine and/or paramagnetic elements such as manganese or gadolinium preferably form part of the molecule.

However, one of the most interesting applications of these bismuth containing compounds is in X-ray imaging. For use as an X-ray contrast agent, it is preferred that the compounds contain bismuth and at least one more heavy atom. The preferred bismuth compounds may in addition to bismuth contain atoms such as bromine, iodine, lanthanides, transition metals, or other metal atoms. Examples include Gd, Ce, Sr, Y, Zr, Ru, Rh, In, Ta, Nb, Dy, Hf, W, I, Mo, Re, Os, Pb, Ba, Ga, Sn, Ha and Tl. Bismuth compounds containing several bismuth and/or several iodine atoms are most preferred. The choice of heavy atom and the number of heavy atoms in each unit are determined by a variety of factors including the toxicity of the overall molecule or cluster complex, the in vitro and in vivo (shelf life) stability of the unit and the X-ray absorption characteristics of the heavy atom. In this regard it should be noted that while the X-ray absorbtion cross section for atoms generally increases with increasing atomic number, the absorption cross section is itself dependent on the X-ray wavelength and increases with increasing photon energy until slightly above a value termed the K-edge whereafter attenuation decreases. Thus there are photon energy ranges for which one element is a better X-ray attenuator than a second even though outside these ranges the second element may be the better attenuator. Consequently the bismuth compounds according to the invention will each have optimum photon energy ranges making them particularly suitable for operation with X-ray imaging apparatus utilizing X-rays having such photon energy ranges. However, by choosing bismuth compounds containing atoms of more than one heavy element one may create X-ray contrast agents having optimal performance in more than one photon energy band or over a broader band. The compounds used according to the present invention are thus particular attractive since they can be selected so as to match their X-ray attenuation profiles with the X-ray emission profiles of particular X-ray sources—in effect the invention provides "tunable" X-ray contrast media. From an efficacy point of view, bismuth and uranium are the heavy atoms with the highest efficacy per atom in all X-ray modalities (CT, plain X-ray and DSA).

In formula I–IV above, $R_1$–$R_5$ may be the same or different and may be any group forming a hydrolytically stable bond to bismuth. Typical $R_1$–$R_5$ groups can for example be aryl groups, optionally substituted with one or more heavy atoms such as Bi and I. For extracellular X-ray contrast agents the $R_{1-5}$ groups are usually substituted with one or more (preferably more) hydrophilic groups. Such compounds should in general have a low charge or preferably no charge.

The bond from bismuth to one of the $R_{1-5}$ groups may for example be of the following types: Bi—C, Bi—O, Bi—S and Bi—N. Some of these bonds are more stable than others and it is known in the literature on the chemistry of bismuth that the stability of the bismuth molecule is very dependent on the chemical nature of this bond and the substituents (see for example Chapter 28 in G. Wilkinson (ed) Comprehensive Coordination Chemistry; Gmelin Handbuch der Anorganischen Chemie Volume 47; L. D. Freedman and G. O. Doak in Chem. Rev (1982) 82 15–57; Methoden der Organischen Chemie (Houben-Weyl) Volume XIII/8; Comprehensive Organometallic Chemistry, Chapter 13; Kirk-Othmer: Encyclopedia of Chemical Technology Volume 3 p 921–936).

Some trialkylbismuth compounds are known to be very hydrolytically unstable, however, we have shown that tri-arylbismuth compounds are surprisingly stable against hydrolysis: triphenylbismuth dissolved in aqueous (25%) tetrahydrofuran is stable under reflux for many days. When the $R_{1-5}$-groups form Bi—C bonds, aryl grou7ps are generally preferred. At least one of the $R_{1-5}$-groups should be an aryl group or substituted aryl group. The term "aryl group" here means any aromatic hydrocarbon ring system or aromatic heterocyclic system. Typical ring systems include for example benzene, naphthalene, indene, fluorene, phenalene, phenanthrene, anthracene, fluoranthene, acephenanthrylene, aceanthrylene, triphenylene, pyrene, chrysene, naphthacene, pleiadene, picene, perylene, pentaphene, pentacene, tetraphenylene, hexaphene, hexacene, rubicene, coronene, trinaphthylene, heptaphene, rubicene, coronene, heptacene, pyranthrene, ovalene, furan, thiophene, thianthrene, pyran, isobenzofuran, chromene, xanthene, phenoxathin, pyrrole, imidazole, pyrazole, isothiazole, isoxazole, pyridine, pyrazine, pyrimidine, pyradizine, indolizine, isoindole, indole, indazole, purine, quinolizine, isocaunoline, quinoline, phtalazine, naphyhyridine, quinoxaline, quinazoline, cinnoline, pteridine, carbazole, β-carboline, phenanthridine, acridine, permidine, phenanthroline, phenazine, phenarsazine, phenothiazine, furazan, phenoxazine, isochroman, chroman, indoline and iso-indoline.

Possible alkyl groups include both substituted or unsubstituted lower and higher alkyl, alkoxy, polyalkoxy and alkylaryl groups, or any other groups.

The $R_{1-5}$ groups may be substituted with contrast active elements or contrast active groups and other non-contrast active elements or groups. Typical contrast active elements are listed above. The most preferred contrast active elements for X-ray imaging are iodine and bismuth. Other substituents include fluorine, chlorine, bromine, alkyl, alkoxy, substituted alkyl for example hyd-oxyalkyl or polyhydroxyalkyl, substituted alkoxy for example hydroxyalkoxy or polyhydroxyaloxy, amides including substituted amides such as —$NAcR_6$ and $CONR_7R_8$ where Ac is an acyl group and $R_6R_8$ which may be the same or different represent lower alkyl, $C_{1-4}$-hydroxyalkyl, carboxy- or amino-$C_{1-4}$-alkyl groups or together both $R_7$ and $R_8$ represent a cyclic croup such as —$CH_2CH_2NR_9CH_2CH_2$— where $R_9$ for example, is a $C_{1-4}$ alkyl group optionally substituted by hydroxyl, carbonyl, aryl or amino groups.

Particularly conveniently, the multinuclear bismuth complexes are presented as their chelate complexes containing EDTA or other APCAs. Such chelate complexes are remarkably stable with regard to release of the heavy metal ions. It is particularly preferred that the electrical charge carried by the completing moieties should substantially if not completely balance that carried by the complexed entity; for APCA chelants this may easily be achieved for example by omission, replacement or deactivation (e.g. by ester or amide formation) of one or more of the carboxyl moieties.

Many suitable chelants are widely known or have been described in the literature, especially literature relating to heavy metal detoxification agents, bifunctional chelants and chelate-based contrast agents, e.g. those described in WO-A-89/00557 (Berg) and the documents mentioned therein and in the search report appended thereto, U.S. Pat. No. 4,647,447 (Gries), U.S. Pat. No. 4,826,673(Dean), EP-A-230893 (Felder), EP-A-217577 (Frincke), U.S. Pat. No. 4,652,519 (Warshawsky), U.S. Pat. No. 4,687,659 (Quay), and numerous other recent patent publications of Nycomed AS, Salutar Inc, Schering AG, Squibb, Bracco, Mallinckrodt, Dow and Guerbet.

While polyamines, especially linear or cyclic polyamines, such as ethylenediamine, 1,4,7-triazacyclononane and cyclen, can be used as chelants, in general APCAs are preferred, particularly DTPA, EDTA and derivatives thereof and other cyclic and non-cyclic APCAs as defined in WO-A-89/00557.

Examples of suitable chelnts include compounds of formulae;

(i) (HOOCCH$_2$)$_2$NCH$_2$CH$_2$N(CH$_2$COOH)$_2$ (ii) (HSCH$_2$CH$_2$)$_2$NCH$_2$CH$_2$N(CH$_2$CH$_2$SH)$_2$ (iii) H$_2$NCH$_2$CH$_2$N(CH$_2$COOH)CH$_2$CH$_2$N(CH$_2$COOH)CH$_2$CH$_2$NH$_2$ (iv) H$_2$NCH$_2$CH$_2$N(CH$_2$CH$_2$SH)CH$_2$CH$_2$N(CH$_2$CH$_2$SH)CH$_2$CH$_2$NH$_2$ (v) HOOCCH$_2$(NCH$_2$CH$_2$)$_3$NCH$_2$COOH (vi) HSCH$_2$CH$_2$(NCH$_2$CH$_2$)$_4$SH (vii) 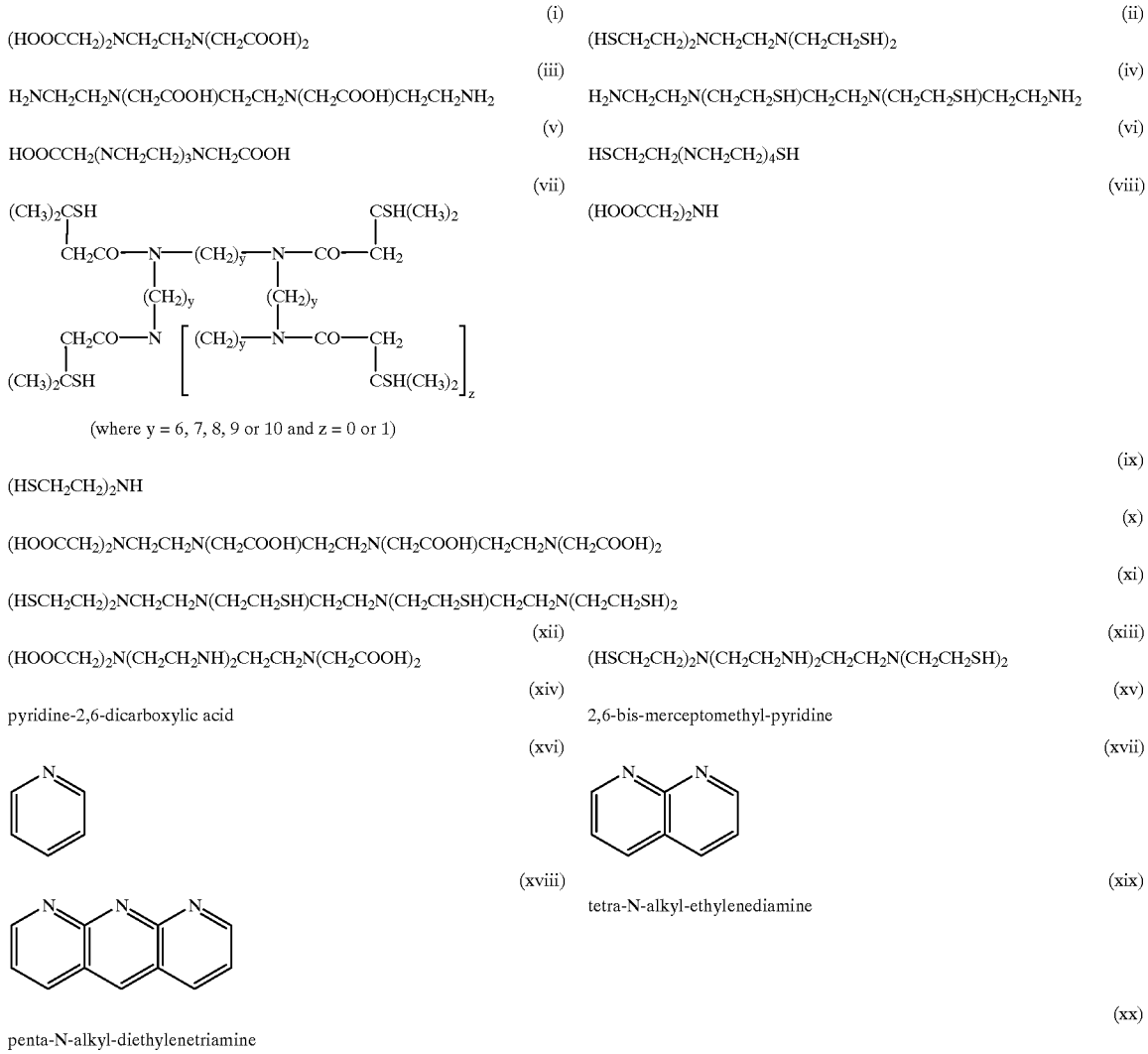

(where y = 6, 7, 8, 9 or 10 and z = 0 or 1)

(viii) (HOOCCH$_2$)$_2$NH (ix) (HSCH$_2$CH$_2$)$_2$NH (x) (HOOCCH$_2$)$_2$NCH$_2$CH$_2$N(CH$_2$COOH)CH$_2$CH$_2$N(CH$_2$COOH)CH$_2$CH$_2$N(CH$_2$COOH)$_2$ (xi) (HSCH$_2$CH$_2$)$_2$NCH$_2$CH$_2$N(CH$_2$CH$_2$SH)CH$_2$CH$_2$N(CH$_2$CH$_2$SH)CH$_2$CH$_2$N(CH$_2$CH$_2$SH)$_2$ (xii) (HOOCCH$_2$)$_2$N(CH$_2$CH$_2$NH)$_2$CH$_2$CH$_2$N(CH$_2$COOH)$_2$ (xiii) (HSCH$_2$CH$_2$)$_2$N(CH$_2$CH$_2$NH)$_2$CH$_2$CH$_2$N(CH$_2$CH$_2$SH)$_2$ (xiv) pyridine-2,6-dicarboxylic acid (xv) 2,6-bis-merceptomethyl-pyridine (xvi)

(xvii)

(xviii)

(xix) tetra-N-alkyl-ethylenediamine (xx) penta-N-alkyl-diethylenetriamine and the phosphorus analogues of these nitrogen-donor based ligands.

Chelants such as NTA, IDA, EDTA, HEDTA, DTPA, DTPA-BMA, HEDDA, TTDA, EDTA-BMA, TBEDDA, MEEDDA, TTHA, EDDA, EHPG, PDTA, CHDTA, HPDTA and triazacyclononane monoacetic acid, especially PDTA and EDTA, are of particular interest.

Particularly preferred chelants include cyclen, EDTA, DTPA, DOTA, DO3A, HP-DO3A, the 6-oxa and 6-thia analogues of DTPA and amides thereof, e.g. DTPA-BMA and DTPA-BMO (6-carboxymethyl-3,9-bis (morpholinocarbonyl-methyl)-3, 6,9-triazaundecanedioic acid—the Gd(III) chelate of which is sometimes referred to as gadopenamide).

Where the chelant is to be attached to a macromolecule, this may conveniently be any tissue, organ or cell targeting macromolecule, for example a biomolecule such as a protein, an antibody or antibody fragment, or alternatively it may be a biologically relatively inert material such as a polysaccharide or poly-sugar alcohol, e.g. dextran or starch. Such macromolecules are discussed extensively in the recent literature relating to contrast agents.

The bismuth compounds used according to the invention may be ionic or, more preferably, may carry no net charge; most preferably the compound is non-ionic. Moreover they may be water-soluable or, less preferably, water-insoluable. Compounds with low solubility in water could be used as X-ray contrast agents for liver, spleen, lymphatic blood pool and gastrointestinal system imaging. Water-soluble macromolecular bismuth compounds (mw>20000) could be used as blood pool X-ray contrast agents. Any necessary counter-ions should of course most preferably also be physiologically tolerable.

The range of physiologically acceptable counterions for therapeutically active bismuth agents is of course well known to pharmacologists.

Suitable counter-ions include for example protons, alkali and alkaline earth metal ions, e.g. sodium, calcium and magnesium and zinc, ammonium and organic cations (e.g. organic amine cations, iodinated organic amine cations, cuarternary ammonium, pyridinium, meglumine, alkylammonium, polyhydroxy-alkylammonium, baser protonated amino acids etc.), transition metal complex cations and organometallic cations.

Suitable counter-ions also include for example halide (e.g. choride, bromide, iodide and I$_3^-$).

The invention also provides novel covalent non-cluster type bismuth compounds, with the proviso that when the bismuth compound is a triphenyl bismuth compound it contains at least one further heavy atom, or at least one of the phenyl groups is substituted in at least four of its ortho, meta and para positions and the molecule as a whole contains at least one hydroxy group or carboxyl group. Preferably the compounds also contain at least one further covalently bonded bismuth atom or at least one covalently bonded iodine atom.

This invention thus provides new bismuth compounds of formula I which may be represented as follows:

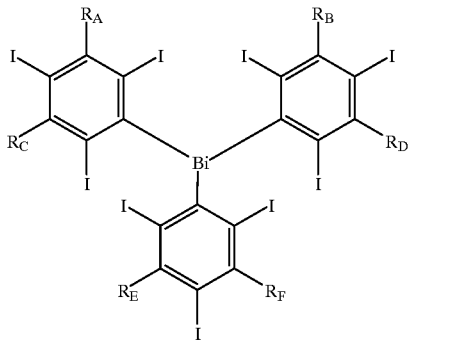
(Ia)

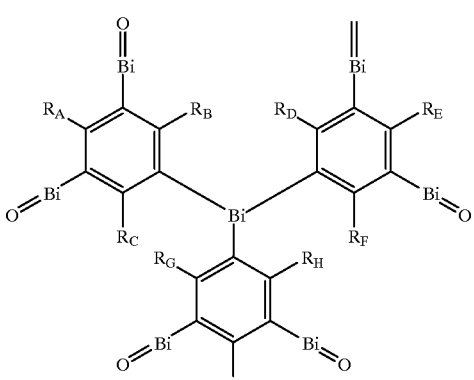
(Ib)

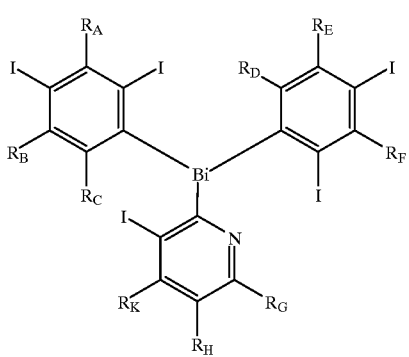
(Ic)

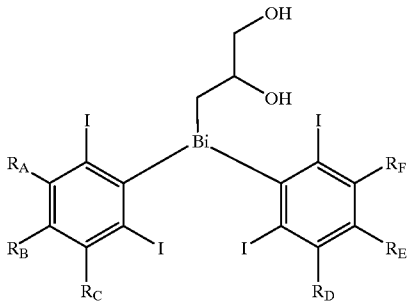
(Id)

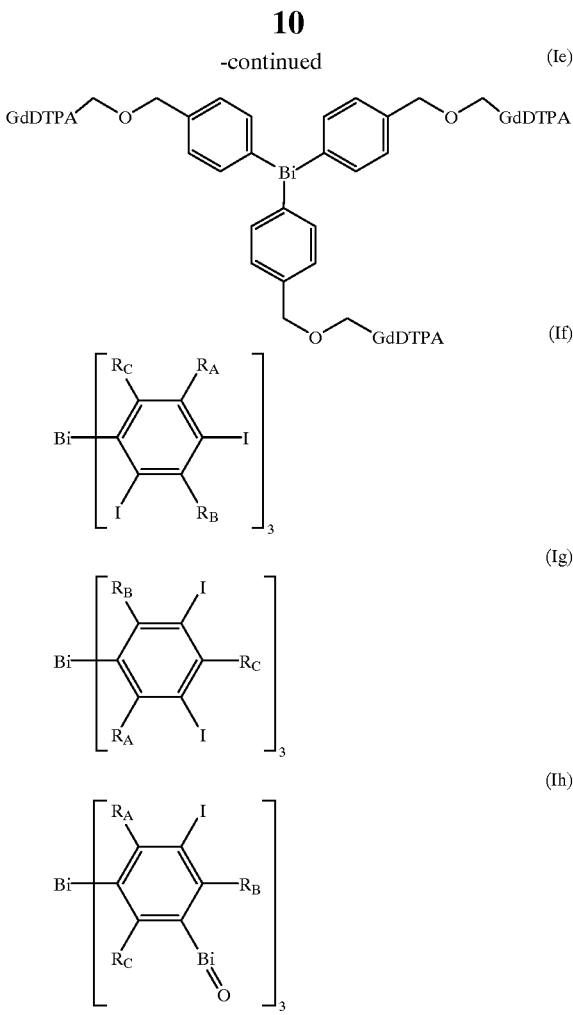
(Ie)
(If)
(Ig)
(Ih)

$R_{A-K}$ in formulae (Ia)–(Ih) can be the same or different. Typical $R_{A-K}$ groups can for example be —COOH, —NHCOCH$_3$, —N(Me)COCH$_3$, —CONHCH$_3$, —CONHCH$_2$Ch$_2$OH, —CONHCH$_2$CONHCH$_3$, NHCOCHOHCH$_3$, —NHCOCH$_2$OCH$_3$, —CONHCH$_2$CHOHCH$_3$OH, —CON(Me)CH$_2$CHOHCH$_2$OH, —CONHCH(CH$_2$CH$_2$OH)$_2$, —CONHCH(CH$_2$OH)$_2$ CHOHCH$_2$OH, —CONHCH(CH$_2$OH).CHOH. CHOH.CH$_2$OH, —OCH$_2$CH$_2$OH, —NHCOCH$_2$OH, —CH$_2$OH and N(COCH$_2$OH)(CH$_2$CH$_2$OH).

This invention also provides new bismuth compounds of formula II which may be represented as follows:

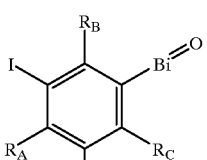
(IIa)

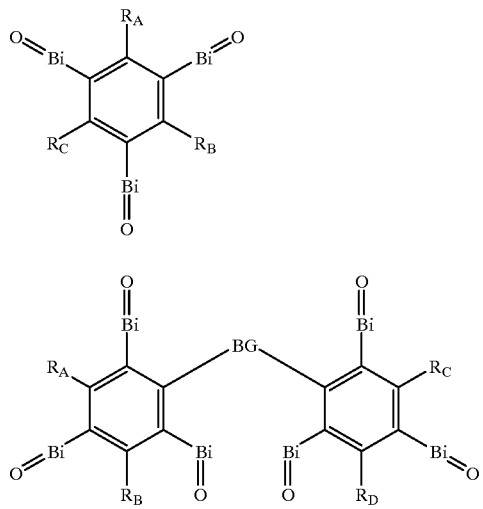

(IIb)

(IIc)

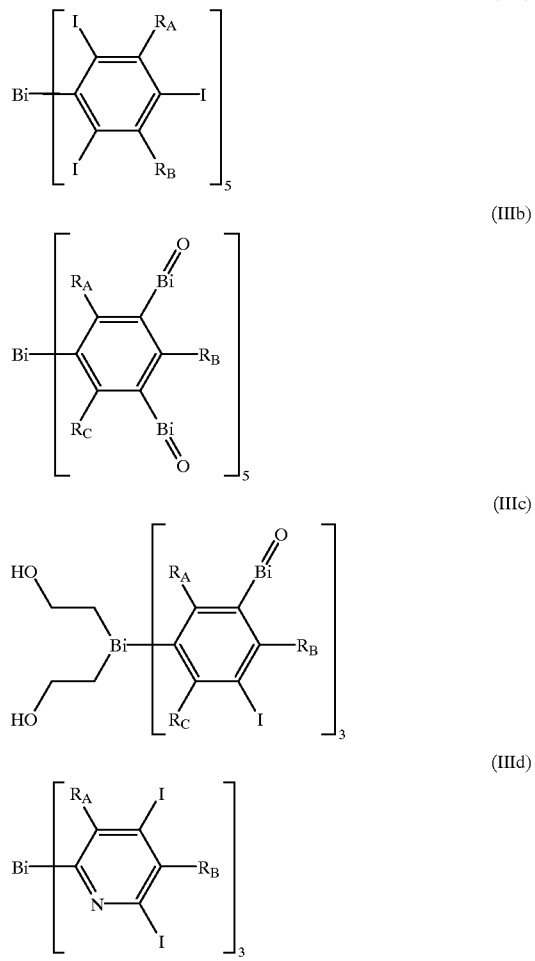

(IIIa)

(IIIb)

(IIIc)

(IIId)

$R_A$–$R_D$ in formulae (IIa)–(IIc) can be the same or diferent and typical $R_{A-D}$ groups are listed above. BG can be any bridging group. In the compounds of the invention, the linker group BG is conveniently a 1, 2 or 3 membered chain comprising carbon, nitrogen, oxygen or sulphur atoms, e.g. a O, S, N or C one atom chain, a NN, NC, NS, CC or CO two atom chain, or a NCN, OCN, CNC, OCO, NSN, CSN, COC, OCC or CCC three atom chain, for example:

- an oxygen atom or a group $NR^1$, CO, $SO_2$ or $CR_2^1$;
- a group COCO, $CONR^1$, $COCR_2^1$, $SOCR_2^1$, $SO_2NR^1$, $CR_2^1CR_2^1$, $CR_2^1NR^1$ or $CR_2^1O$;
- a group $NR^1CONR^1$, $OCONR^1$, $CONR^1CO$, $CONR^1CR^1_2$, OCOO, $CR^1_2OCR^1_2$, $OCR^1_2CO$, $CR^1_2CONR^1$, $CR^1_2CR^1_2CR^1_2$, $COCR^1R^1CO$, $CR^1_2NR^1CR^1_2$, $CR^1_2SO_2NR^1$, $CR^1_2OCO$, or $NR^1SO_2NR^1$;
where $R^1$ is hydrogen or a $C_{1-6}$-alkyl or alkoxy group optionally substituted by hydroxy, alkoxy, oxa or oxo (e.g. a polyhydroxyalkyl, formyl, acetyl, hydroxyl, alkoxy or hydroxyalkoxy group), or where attached to a carbon $R^1$ may also be a hydroxyl group.

Advantageously, the BG group is not symmetrical. This may be achieved for exaple by asymmetrical substitution of a symmetrical chain (e.g. N—C—N substituted as $NHCONR^1$) or by selection of an asymmetric chain (e.g. OCN substituted as $OCONR^1$). In particular, it is preferred that the linker group BG should be polar and also that it should be hydrophilic.

Other examples of bridging groups include —NHCO$(C_2)_n$ CONH—, —NHCO—$(CH_2OCH_2)_n$—CONH—, —NHCOCH$_2$(CH$_2$OCH$_2$)$_n$CH$_2$CONH—, —CONHCH$_2$—(CHOH)$_n$CH$_2$NHCO—, —NH(Ac)CH$_2$(CHOH)$_n$CH$_2$N(Ac)— and —NHCOCH$_2$CH$_2$SCH$_2$CH$_2$CONH— where n is an integer between 1 and 6.

This invention further provides new bismuth compounds of formula III which may be represented as follows:

The $R_A$–$R_C$ groups in each of the molecules (for example in IIIa) may be the same or different and typical $R_A$–$R_c$ groups are described above.

This invention also provides new bismuth compounds of formula IV which may be represented as follows:

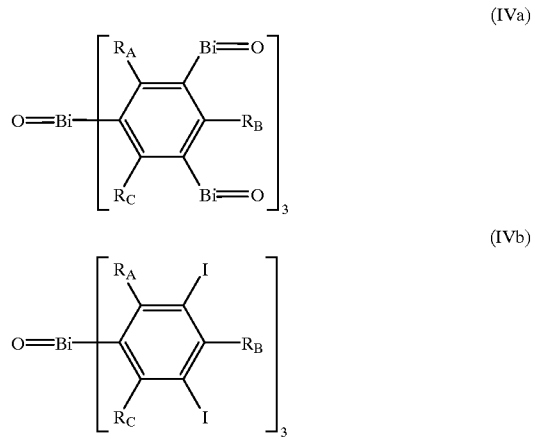

(IVa)

(IVb)

The $R_A$–$R_C$ groups in each of the above molecules. (for example in IVa) may be the same or different and typical $R_A$–$R_C$ groups are described above.

Bismuth compounds of formula V can be represented for example by the following cores:

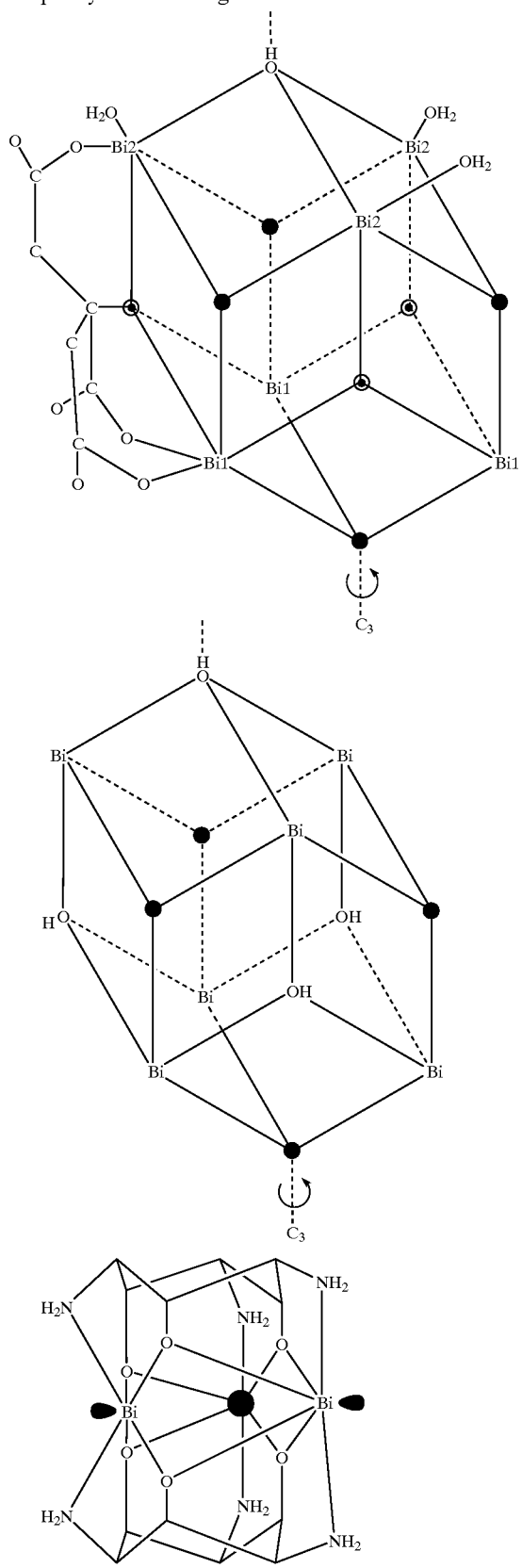

The bismuth compounds can be prepared from cheap and easily available bismuth salts. The general synthesis of covalent bismuth compounds is well described in the above cited reviews on bismuth chemistry.

Thus for example, bismuth compounds of formula I can be synthesized from bismuth (III) chloride as follows:

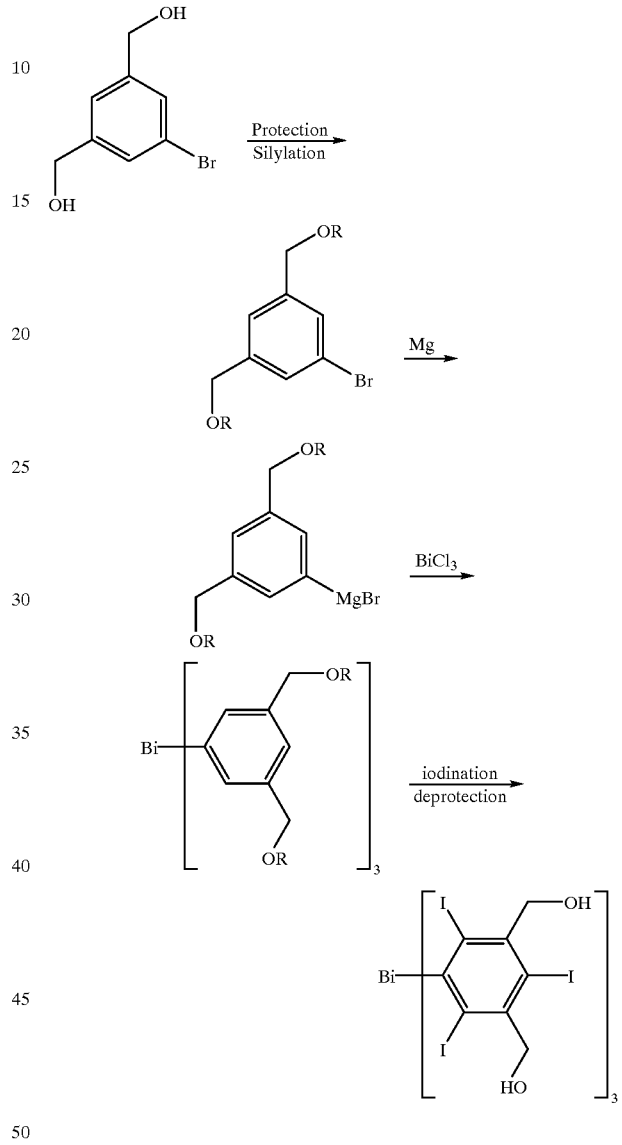

Bismuth compounds of formula II may for example be synthesized from triiodinated X-ray contrast agent derivatives and bismuthoxychloride as follows:

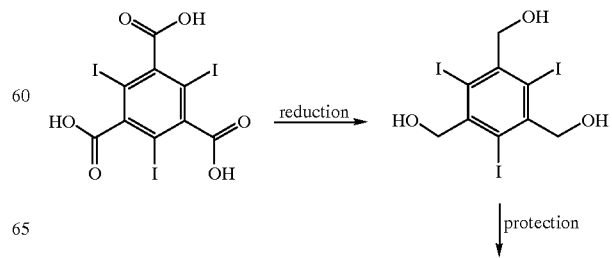

-continued

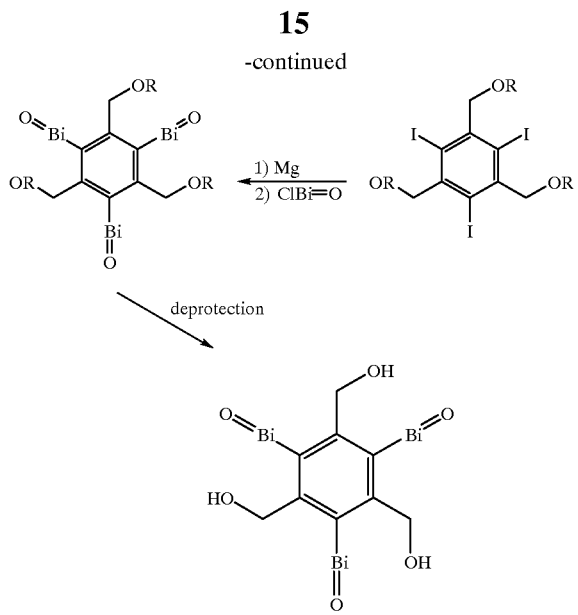

Bismuth compounds of formula III (with bismuth oxidation number 5) may be prepared by halogenation of bismuth compounds of formula I followed by a Grignard reaction or using another organometallic reagent such as the lithium salt as illustrated below:

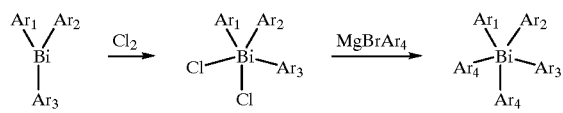

Bismuth comounds of formula IV may be prepared from the dichlorides as follows:

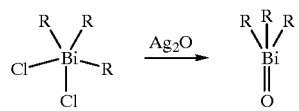

For administration to human or animal subjects, the bismuth compounds will conveniently be formulated together with pharmaceutical or veterinary carriers or excipient. The contrast media of the invention may conveniently contain pharmaceutical or veterinary formulation aids, for example stabilizers, antioxidants, osmolality adjusting agents, buffers, pH adjusting agents, colorants, flavours, viscosity adjusting agents and the like. They may be in forms suitable for parenteral or enteral administration, for example, injection or infusion or administration directly into a body cavity having an external voidance duct, for exlmpie the gastrointestinal tract, the bladder and the uterus. Thus the media of the invention may be presented in conventional pharmaceutical administration forms such as tablets. coated tablets, capsules, powders, solutions and suspensions although dispersions in physiologically acceptable carrier media, e.g. water for injections, will Generally be preferred. Where the medium is formulated for parenteral administrator, the carrier medium incorporating the bismuth compound is preferably isotonic or somewhat hypertonic. Moreover, media for parenteral administration may contain small quantities, e.g. 0.01 to 10 mole percent relative at the bismuth compound, of free chelants or weak chelate complexes with physiologically tolerable chelated species (e.g. $Ca^{2+}$); small additions of sodium or calcium salts may also advantageously be made.

For use in X-ray imaging the media of the invention should generally have a heavy atom content of 1 millimole/1 to 5 mole/1, preferably 0.1 to 2 mole/1. Dosages of from 0.05 to 2.0 mmoles/kg, e.g. 0.5 to 1.5 mmoles/kg, will generally be sufficient to provide adequate contrast although dosages of 0.8 to 1.2 mmoles/kg will normally be preferred.

For scintigraphy, dosages of the radioactive species will generally be significantly lower.

Polymers with the bismuth compounds incorporated, for example bound to the polymer molecules, may be used in medical catheters.

Thus in summary the present invention provides a particularly effective means by which contrast media efficiency may be enhanced by increasing the relative proportion of molecular volume that is occupied by the contrast enhancing heavy or paramagnetic metal atom. For X-ray contrast media in particular, this also enables higher K-edge value atoms than the iodine of the now conventional X-ray contrast media to be utilized effectively.

The present invention will now be illustrated further by the following non-limiting Examples (all ratios and percentages are by weight and all temperatures are in degrees Celsius unless otherwise specified):

INTERMEDIATE 1

4-Bromo-1-(2,5-dimethylpyrrolo) benzene

The title compound was prepared according to Bruekelman et al. in *J. Chem Soc Perkin Trans I* (1984) 2801.

INTERMEDIATE 2

2-(4-Bromophenyl)-4-dimethyl-2-oxazoline

4-Bromobenzoic acid (25.32 g, 126 mmol) and thionyl chloride (54 ml) were stirred in benzene (250 ml) under reflux for 24 hours. The solvent was removed at reduced pressure, and the formed product, 4-bromobenzoyl chloride, purified by distillation. Yield 23.30 g (88%), b.p. 82–84° C. (1 mmHg).

4-Bromobenzoyl chloride (20.02 g, 91 mmol) was dissolved in dichloromethane (180 ml) and added dropwise to a solution of 2-amino-2-methyl-1-propanol (19.20 g, 216 mmol) in dichloromethane (90 ml) at ambient temperature. The mixture was stirred for 24 hours at ambient temperature, followed by filtration and removal of the solvent at reduced pressure. Thionyl chloride (90 ml) was added dropwise and the mixture was stirred for 30 minutes at ambient temperature. Excess thionyl chloride was removed at reduced pressure and the residue was added to an aqueous HCl-solution (5%, 500 ml). The solution was washed with ether (2×100 ml) and aqueous NaOH (50%) was added to pH 9. The basic solution was extracted with ether (3×100 ml), and the combined ether solution was washed with water (50 ml) and saturated aqueous NaCl-solution. The dried ($MgSO_4$) ether solution was evaporated and the title compound isolated by distillation. Yield 14.14 g (61%), b.p. 128–130° C. (1 mm Hg).

$^1$H NMR (200 MHz, $CDCl_3$): δ 1.32 (s, 6H), 4.05 (s, 2H), 7.47 (d, 2H), 7.75 (d, 2H).

INTERMEDIATE 3

1,2- Bis(dimethylsilyl)benzene 1,2-Dibromobenzene (9.37 g, 40 mmol) in dry tetrahydrofuran (25 ml) was added dropwise to a stirred solution of dimethylchlorosilane (7.67 g, 81 mmol), magensium (2.00 g, 82 mmol) and one crystal of iodine in dry tetrahydrofuran (150 ml). The mixture was heated at reflux for 4 hours, washed with aoueous HCl (100 ml, 2 M) and then with water (3×50 ml). The organic solution was dried (MgSO$_4$), the solvent was evaporated and the title product isolated by distillation. Yield 3.87 g (50%), b.p. 54–56° C., Rf: 0.69 (silica, hexane:ether=1:1), MS(EI): 194 (M$^+$).

INTERMEDIATE 4

4-Bromo-N,N-(1,2-bis(dimethylsilyl)benzene)aniline

Cesium fluoride (2.19 g, 14.4 mmol) was added to a stirred solution of 1,2-bis(dimethylsilyl)-benzene (Intermediate 3) (3.90 g, 20 mmol) in 1,3-dimethyl-3,4,5,6-tetrahydro-2(1H)-pyrimidinone (60 ml) at ambient temperature. The mixture was stirred for 4 hours at 120° C. The cooled reaction mixture was poured into hexahe/ether (60 ml, 1:1), washed with phosphate buffer at pH7 (3×10 ml) and dried (MgSO$_4$). The solvent was evaporated at reduced pressure and the residue was recrystallized from methanol/ether. Yield: 1.58 g (27%), MS (EI): 361/363.

INTERMEDIATE 5

Dimethyl-t-butylsilylether of 4-bromo-benzyl alcohol

Dimethyl-t-butylsilyl chloride (9.58 g, 65 mmol) was added to a solution of 4-bromobenzyl alcohol (10.0g, 53 mmol) and imidazole (9.02 g, 133 mmol) in dry dimethylformamide (50 ml). The mixture was stirred at ambient temperature for 10 hours. Ether (25 ml) and water (25 ml) was added and after separation of the phases, the organic phase was washed with water, dried (MgSO$_4$) and evaporated. Yield 14.3 g (90%).

EXAMPLE 1

Triphenylbismuth suspension

Human serum albumin (HSA) (3 g) is dissolved in distilled water (150 ml). The solution is filtered through a membrane filter with pore size 0.45 micron. A filtered solution (0.22 micron) of triphenylbismuth (Fluka) (1.0 g) in 96% ethanol (25.0 ml) is slowly added to the HSA solution under vigorous stirring over a prolonged period of time. The microparticles formed are centrifuged and are washed repeatedly. The particles are dispersed in a sterile filtered isotonic 0.9% sodium chloride/water for injection solution (100 ml) under vigorous stirring until a homogeneous suspension is achieved.

EXAMPLE 2

Freeze dried powder comprising tris(4-carboxyphenyl)bismuth trisodium salt for dissolution in water prior to injection Tris(4-carboxyphenyl)bismuth is prepared according to Supniewski, J. in Rocniki Chem 6 (1926) 97, and the compound (5.0 g) is dissolved in water by addition of three equivalents of sodium hydroxide. The solution is filled into a 50 ml vial and freeze dried.

EXAMPLE 3

Dodecafluorodibismatriptycene (C$_{18}$Bi$_2$F$_{12}$) suspension

A filtered solution of dodecafluorodibismatriptycene (0.6 g) in tetrahydrofuran (20.0 ml) is slowly added to an aqueous HSA/propylene glyco solution under vigorous homogenizing.

The microparticles formed are centrifuged and are washed repeatedly before the particles are dispersed in a sterile solution of 0.05% polysorbate 80 in saline (5.3 ml).

EXAMPLE 4

Tris (4-hydroxymethylphenyl) bismuthine

Trimethylsilyl chloride (1.9 ml, 15 mmol) was added dropwise to a stirred solution of 4-bromobenzyl alcohol (2.0 g, 11 mmol) in toluene (25 ml) and pyridine (2 ml) at 0° C. The stirred mixture was heated to ambient temperature during 3 hours. The reaction mixture was filtered and the organic solution evaporated to yield pure 4-bromobenzyl trimethylsilyl ether. The silyl ether can be further purified by distillation (b.p. 73° C., 0.1 mm Hg). Yield after distillation: 1.49 g (50%)

The above silyl ether (1.49 g, 5.5 mmol) in tetrahydrofuran (10 ml) was added dropwise to a stirred mixture of magnesium turnings (0.13 g, 5.5 mmol) in tetrahydrofuran (20 ml) containing a few crystals of iodine. The mixture was heated at reflux until all magnesium was dissolved. Bismuth (III) bromide (0.62 g, 1.4 mmol) was gradually added and the reaction mixture was heated to reflux for 2 hours. The cooled mixture was filtered through a plug of celite followed by addition of dry tetrabutylammonium fluoride (1.46 g, 5.6 mmol) at 0° C. The stirred reaction mixture was heated to room temperature during 2 hours followed by evaporation of the solvent. Chloroform (20 ml) and water (10 ml) were added to the residue and the title compound precipitated out as a white crystalline material. The product was washed with chloroform. Yield 0.22 g (30%) m.p.>300° C.

$^1$H NMR (200 MHz, DMSO-d$_6$): δ 4.47 (d, 2H), 5.15 (t, 1H) 7.3(d, 2H) and 7.70 (d, 2H).

EXAMPLE 5

Tris(4-hydroxyphenyl)bismuthine

Trimethylsilyl chloride (11 ml, 87 mmol) was added dropwise to a stirred solution of 4-bromophenol (10.0 g, 58 mmol) in toluene (25 ml) and pyridine (20 ml) at a 0° C. The stirred mixture was heated to ambient temperature during 3 hours. The reaction mixture was filtered and the organic solution evatorated to yield pure 4-bromophenyl trimethylsilyl ether. The silyl ether can be further purified by distillation (b.p. 122° C., 20 mmHg). Yield after distillation: 13.70 g (75%).

The above silyl ether (13.70 g 43 mmol) in tetrahydrofuran (25 ml) was added dropwise to a stirred mixture of magnesium turnings (1.06 g, 43 mmol) in tetrahydrofuran (25 ml) containing a few crystals of iodine. The mixture was heated at reflux until all magnesium was dissolved. Bismuth (III) bromide (4.82 g, 11 mmol) was gradually added and the reaction mixture was heated to reflux for 2–3 hours. The cooled mixture was filtered through a plug of celite followed by addition of dry tetrabutylammonium fluoride (11.5 g, 44 mmol) at 0° C. The stirred reaction mixture was heated to room temperature during 2 hours followed by evaporation of the solvent. Chloroform (20 ml) and water (10 ml) were added to the residue and the title compound precipitated out as a white crystalline material. The product was washed with cold chloroform. Yield 1.59 g (22.5%) mp>300° C.

$^1$H NMR (200 MHz, DMSO) 6.87 (d, 2H), 8.20 (d, 2H), 9.35 (s, 1H).

EXAMPLE 6

Tris(4-(2,5-dimethylpyrrolo)phenyl) bismuthine n-Butyllithium in hexane (13.5 ml, 1.5 M, 20 mmol) was added dropwise to a stirred solution of 4-bromo-1-(2,5- dimethylpyrrolo) benzene (Intermediate 1) (5.0 g, 20 mmol) in tetrahydrofuran (75 ml) at −78° C. under an atmosphere of dry argon. After 10 minutes, the solution was heated to −30° C. followed by dropwise addition of a solution of bismuth (III) bromide (2.15 g) in tetrahydrofuran (10 ml). The mixture was stirred for 2.5 hours during heating to room temperature, filtered and the organic solution was evaporated. The residue was recrystallized from benzene. Yield 2.40 g (70%), white crystalline material, m.p.>300° C. (decomposed).

$^1$H NMR (300 MHz, CDCl$_3$): δ 2.06 (s, 18H), 5.91 (s, 6H), 7.28 (d, 6H), 7.88 (d, 6H).

EXAMPLE 7

Tris (4-(4,4-dimethyl-2-oxazoline) bismuthine 2-(4-Bromophenyl)-4-dimethyl-2-oxazoline (Intermediate 2) (13.93 g, 55 mmol) dissolved in dry tetrahydrofuran (75 ml) was added dropwise to a suspension of magnesium turnings (1.34 g, 55 mmol) and one crystal of iodine in tetrahydrofuran (100 ml). The reaction mixture was stirred until all the magnesium turnings dissolved. The mixture was stirred for another hour at ambient temperature followed by dropwise addition of bismuth (III) bromide (6.34 g, 13.8 mmol) in dry tetrahydrofuran (10 ml). The reaction mixture was stirred at 55° C. under an argon atmosphere overnight, followed by filtration through a plug of celite and added to ice-water (200 ml). The mixture was extracted with ethyl acetate (3×100 ml), the combined organic phase was dried (MgSO$_4$), evaporated and the residual material subjected to flash chromatography on silica using ethyl acetate: yield 7.48 g (72%), Rf: 0.25 (silica, ethyl acetate), white crystalline material m.p. 233–234° C.

$^1$H NMR (300 MHz, CD$_3$OD). δ 1.34 (s,18H), 4.14 (s, 6H), 7.80 (d, 6H), 7.87 (d, 6H).

EXAMPLE 8

Tris (4-bromophenyl) bismuthine n-Butyllithium in heptane (2.7 M, 9.25 ml, 50 mmol) was added dropwise to a solution of 1,4-dibromobenzene (5.90 g, 50 mmol) in dry tetrahydrofuran (250 ml) under an atmosphere of dry argon at −78° C. The mixture was stirred for 1 hour at −78° C. A solution of bismuth (III) bromide (2.92 g, 12.5 mmol) in dry tetrahydrofuran (20 ml) was slowly added and the mixture was stirred overnight. After filtration through a plug of celite, the solvent was removed at reduced pressure, and the residue subjected to flash chromatography on silica gel using dichloromethane hexane (20:80); yield: 3.05 g (72%), Rf: 0.40 (silica, dichloromethane: hexane (20.80).

$^{13}$C NMR (200MHz, CDCl$_3$): δ 122.89, 133.78, 139.02 and 153.30.

EXAMPLE 9

Tris (4-ethyloxycarbonylphenyl) bismuthine n-Butylithium in heptane (4.89 ml, 2.7 M, 13.2 mmol) was dropwise added to a stirred solution of tris (4-bromophenyl) bismuthine (from Example 8) (2.71 g, 4 mmol) in dry tetrahydrofuran (40 ml) under an atmosphere of argon at −78° C. The mixture was stirred overnight followed by filtration through a plug of celite and poured into water (50 ml). The mixture was extracted with ethyl acetate (3×50 ml), the combined organic solution was dried (MgSO$_4$) and the solvent evaporated at reduced pressure. The white powder was purified by flash chromatography to yield 1.03 g (52%) of the title compound as a white crystalline powder.

$^1$H NMR (200 MNz, CDCl$_3$). δ 1.36 (t, 9H), 4.35 (q, 6H) 7.54 (d, 6H) and 7.88 (d, 6H).

EXAMPLE 10

Tris (4-hydroxyphnyl) bismutbine dihromide

Bromine (3 mmol, 0.16 ml) was added dropwise to a stirred mixture of tris (4-hydroxyphenyl) bismuthine (Example 5) (1.5 g, 3 mmol) in methanol (25 ml) at 0° C. The mixture was stirred for 1 hour at ambient temperature. The solvent was removed under reduced pressure. The residue was washed with chloroform and the title compound isolated as a white crystalline material. Yield: 1.20 g (62%).

$^1$H NMR (300 MHz, DMSO-d$_6$) 7.09 (d, 2H), 9.00 (d, 2H), 9.43 (s, 1H).

EXAMPLE 11

Tris (3,5-diiodo-4-hydroxy phenyl) bismuthine dibromide

Benzyltrimethylammonium dichloroiodate (prepared according to Kajigaeshi et al. in *Chem Lett.* (1987) 2109 (3.49 g, 10 mmol) and sodium hydrogen carbonate were added to a solution of tris (4-hydroxyphenyl) bismuthine dibromide (Example 10) (1.0 g, 1.54 mmol) in a mixture of dichloromethane and methanol (30 ml, 2:1) at ambient temperature. The mixture was stirred for 24 hours at ambient temperature. Ether (100 ml) was added and the organic solution with precipitate was washed with water, and the title compound was isolated as a white crystalline powder. Yield 0.43 g (20%). MS showed peak m/e 209 (Bi) $^1$H NMR (300 MHz), DMSO-d$_6$) 7.53 (s)

EXAMPLE 12

BiDTPA-aminoethyl dextran for X-ray blood pool imaging

Bisanhydride of DTAA (3.25g) (prepared from DTPA according to Eckelman in *J. Pharm. Sci.* 64 (1975) 704) was gradually added to a solution of aminoethyl dextran (MW 80,000, 5.0 g) in dry dimethylsulphoxide (400 ml) at ambient temperature. The mixture was stirred for 20 hours at the same temperature followed by addition of water (700 ml). The pH value was adjusted to 5.5, a solution of bismuth (III) nitrate pentahydrate (4.85 g, 10 mmol) in water (50 ml) was added, the pH value was adjusted to 4.8 and the solution was dialyzed against 0.9 ak (w/v) NaCl for one week. The aqueous solution was evaporated and the product was dried in vacuum at 50° C. Yield: 7.2 g white solid material containing 6.0% bismuth.

EXAMPLE 13

Bismuth (III) chelate of 18-[{3-(2-carboxybutyl)-2, 4,6-trifodophenyl}amino]-3,6,9-tris(carboxymethyl)-11,18-dioxo-2,6,12-tetraazaoctadecanoic acid The chelating agent above (prepared according to WO94/27644)(20.3 g, 0.02 mol) is dissolved in water (800 ml). Freshly precipitated bismuth hydroxide (0.02 mol) (prepared from bismuth nitrate pentahydrate and sobium hydroxide) is added and the mixture is stirred at 100° C. for 24 hours. The solvent is evaporated at reduced pressure and the title compound is isolated as a white crystalline material.

EXAMPLE 14

Tris (2,4,6trimethylphenyl)bismuthine

The compound was prepared according to Matano et al. in Bull Chem Soc. Jpn, 65 3504 (1992). Yield: 771%

EXAMPLE 15

Tris(2,4,6trimethylphenyl)bismuthine dichloride

Thionyl chloride (1.48 g, 11 mmol) was added to a solution of tris(2,4,6-trimethylphenyl)bismuthine (Example 14) (5.66 g, 10 mmol) in hexane (100 ml) at ambient temperature. The mixture was stirred for one hour and the precipitated product was isolated and recrystalized from ethanol. Yield: 5.70 g (90%).

$^1$H NMR (300 MHz, CDCl$^3$): 2.32 (9H), 2.74 (18H), 7.16 (6H).

EXAMPLE 16

Triphenylbismuthine difluoride

The compound was prepared according to Challenger and Wilkinson in *J. Chem Soc.* 121: 91 (1922). Yield: 75%.

EXAMPLE 17

Tris(2,6-dimethylphenyl)bismuthine

2-Bromo-m-xylene (9.25 g, 50 mmol) in ether (15 ml) was added dropwise to a stirred suspension of magnesium (1.22 g, 50 mmol) and some crystals of iodine in ether (20 ml) at 0° C. When the Grignard reagent was formed (4 hours), the mixture was stirred at ambient temperature for one hour. Bismuth chloride (3.15 g, 10 mmol) was added and the mixture was stirred for 10 hours. The reaction mixture was poured into sat,rated ammonium chloride solution an extracted with ether (3×20 ml) The combined organic phase was cried (MgSO$_4$) and the solvent evaporated at reduced pressure. The title compound was recrystallised from ethanol. White solid, yield: 1.81 g (35%).

$^{13}$C NMR (200 MHz CDCl$_3$) δ 28.53, 127.17, 127.52, 145.05, 158.42.

EXAMPLE 18

Tris(4-aminophenyl)bismuthine protected with 1,2-bis(dimethylsilyl) benzene n-Butyllithium in hexane (2.50 ml, 1.6M, 4 mmol) was added dropwise to a stirred solution of 4-bromo-N,N-(1,2-bis(dimethylsilyl)benzene)aniline (Intermediate 4)(1.45 g, 4 mmol) in tetrahydrofuran at −78° C. The mixture was stirred for 1 hour, a solution of bismuth bromide (0.45 g, 1 mmol) in tetrahydrofuran (10 ml) was added and the reaction mixture was stirred overnight. The mixture was poured into phosphate buffer pH 7 (50 ml), the acueous phase was extracted with chloroform (3×50 ml), the combined organic phases (tetrahydrofuran and chloroform) was dried (MgSO$_4$) and the solvents evaporated at reduced pressure. The product was recrystallised from hexane/ether and isolated as a white crystalline material. Yield: 0.60 g (57%). Anal.: C: 54.51%, H: 5.79%, H: 4.09% (Calculated: C: 54.57%, H: 5.72%, N: 3.98%)

EXAMPLE 19

Bis(4-hydromethylnhenyl)bismuth bromide as bis trimethyl-t-butyl ether

Bismuth tribromide (0.9 g, 2.1 mmol) was added to a solution of silylether (Intermediate 5) (5.62 g, 6.4 mmol) in tetrahydrofuran (25 ml) at ambient temperature. The stirred mixture was refluxed overnight, the solvent was evaporated at reduced pressure and the title compound was purified on flash chromatography (silica, hexane:ethyl-acetate 8:1). Yield 1.59 g (35%).

$^1$H NMR (200 MHz, CDCl$_3$): δ 0.17 (s, 12H), 0.99 (s, 18H) 4.80 (s, 4H), 7.65 (d, 4H), 8.20 (d, 4H)

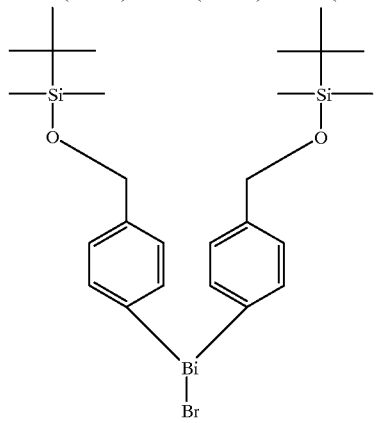

EXAMPLE 20 p-Phenylene-bis (di(4-hydoxymethylelylbismuthin) as dimethyl-t-butylsilyl ether n-Butyllithium in hexane (1.51 ml, 1.6M, 2.4 mmol) was added dropwise to a stirred solution of 1,4-dibromo-benzene (0.26 g, 1.1 mmol) in tetrahydrofuran (15 ml) at −−78° C. The mixture was stirred for 1.5 hour, the silyl ether from Example 19 (1.59 g, 2.2 mmol) in tetrahydrofuran (10 ml) was added and the mixture was warmed up to reflux temperature during one hour. After 10 hours reflux the mixture was extracted with aqueous sodium chloride solution (40 ml, 5%) and extracted with water (2×10 ml). The dried (MgSO$_4$) organic solution was evaporated and the title compound purified by flash chronatography (silica, hexane:ethylacetate 8:2). Yield: 0.67 g (22%).

$^1$H NMR (200 MHz, CDCl$_3$) δ 0.19 (s, 18H), 1.03 (s, 27H), 4.81 (s, 6H), 7.42 (d, 6H), 7.52 (q, 4H), 7.78 (d, 6H).

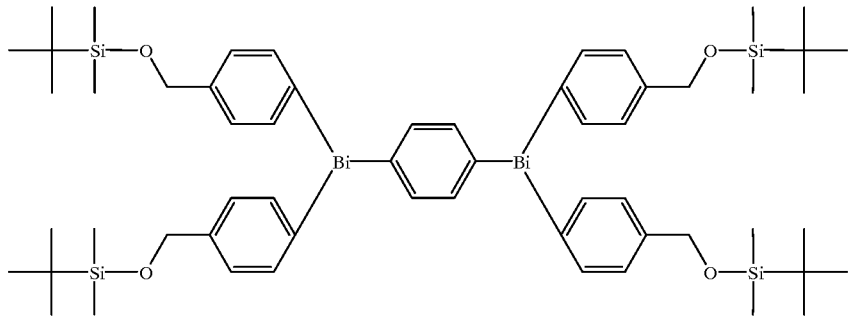

EXAMPLE 21

Preparation of tetrabenzylalcohol from Example 20

The silylether (from Example 20) is cleaved with tetrabutylammonium fluoride in tetrahydrofuran.

EXAMPLE 22

Preparation of tris (4-aminophenyl)bismuthine from Example 18

The silyl-derivative (from Example 18) is cleaved with tetrabutylammonium fluoride according to standard methods in organic chemistry.

EXAMPLE 23

Activity of bismuth compounds against Helicobarter pylori

Various bismuth compounds were tested in different concentrations against *Helicobacter pylori* on agar plates. Minimal Inhibitory Concentrations (MIC—values) are given in mg substance per litre.

| Substance | Example No. | MIC - value |
| --- | --- | --- |
| Tris(2,4,6-trimethylphenyl)-bismuthine chloride | 15 | ≦0.25 |
| Tris(2,4,6-trimethylphenyl)-bismuthine | 14 | ≦0.25 |
| Triphenylbismuthine difluoride | 16 | 8 |
| Tris(2,6-dimethylphenyl)-bismuthine | 17 | 4 |
| Bismuth subsalicylate | — | 4 |
| Bismuth subnitrate | — | 32 |

What is claimed is:

1. A method of treating a gastrointestinal disorder in a human or non-human animal body which method comprises administering to said body a physiologically tolerable dose of a compound selected from formulae I–IV

 (I)

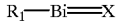 (II)

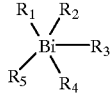 (III)

 (IV)

where the groups $R_1$–$R_5$ may be the same or different and are groups forming a hydrolytically stable bond to bismuth and X is O, S or $NR_6$ where $R_6$ is lower alkyl, substituted lower alkyl or an aryl group.

2. A method as claimed in claim 1 wherein $R_1$–$R_5$ are selected from aryl groups.

3. A method as claimed in claim 2 wherein $R_1$–$R_5$ are optionally substituted benzene.

4. A method as claimed in claim 2 wherein $R_1$–$R_5$ are optionally substituted pyridine.

5. A method as claimed in claim 1 wherein said compound is triphenyl bismuth, tris(4-carboxyphenyl) bismuth, tris(4-hydroxymethylphenyl) bismuthine, tris(4-hydroxyphenyl) bismuthine, tris(4-(2,5-dimethylpyrrolo) phenyl) bismuthine, tris(4-(4,4-dimethyl-2-oxazoline)phenyl) bismuthine, tris(4-bromophenyl) bismuthine, tris(4-ethyloxycarbonylphenyl) bismuthine, tris(4-hydroxyphenyl) bismuthine dibromide, tris(2,4,6-trimethylphenyl) bismuthine, tris(2,4,6-trimethylphenyl) bismuthine dichloride, triphenyl bismuthine difluoride, or tris(2,6-dimethylphenyl) bismuthine.

6. A method as claims in claim 1 wherein the disorder is caused by *Heliobacter pylori*.

* * * * *